US00PP19069P2

(12) United States Plant Patent
Smit

(10) Patent No.: US PP19,069 P2
(45) Date of Patent: Aug. 5, 2008

(54) ***IMPATIENS* PLANT NAMED 'SILTE REDSAR'**

(50) Latin Name: *Impatiens walleriana*
Varietal Denomination: Silte Redsar

(75) Inventor: Erik Smit, Andijk (NL)

(73) Assignee: Goldsmith Seeds Europe B.V., Andhijk (NL)

( * ) Notice: Subject to any disclaimer, the term of this patent is extended or adjusted under 35 U.S.C. 154(b) by 0 days.

(21) Appl. No.: 11/786,131

(22) Filed: Apr. 11, 2007

(51) Int. Cl.
*A01H 5/00* (2006.01)

(52) U.S. Cl. ..... Plt./317
(58) Field of Classification Search ..... Plt./317
See application file for complete search history.

*Primary Examiner*—Kent L. Bell
(74) *Attorney, Agent, or Firm*—Jondle & Associates, P.C.

(57) ABSTRACT

A new *Impatiens* plant particularly distinguished by double, rose-shaped, red and white flowers, semi-compact, upright, outwardly spreading and mounded plant habit, free flowering, good basal branching, and moderately vigorous growth habit, is described.

1 Drawing Sheet

Genus and species: *Impatiens walleriana.*
Variety denomination: 'Silte Redsar'.

BACKGROUND OF THE NEW PLANT

The present invention comprises a new and distinct cultivar of *Impatiens,* botanically known as *Impatiens walleriana,* and hereinafter referred to by the cultivar name 'Silte Redsar'. The new cultivar originated from a hybridization made in June 2004 in Andijk, The Netherlands. The female parent was the proprietary red star-flowered *Impatiens* plant 'ID04-377-1' (unpatented), while the male parent was the proprietary red star-flowered *Impatiens* plant 'ID03-1913' (unpatented). The seeds produced by the hybridization were sown in September 2004. A single plant selection was chosen for further evaluation and for asexual propagation in December 2004.

The new cultivar was created in 2004 and has been asexually reproduced repeatedly by vegetative cuttings and tissue culture in Andijk, The Netherlands and Gilroy, Calif. over a two-year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar were applied for the European Union on Dec. 14, 2006.

SUMMARY OF THE INVENTION

The following are the most outstanding and distinguishing characteristics of this new cultivar when grown under normal horticultural practices in Gilroy, Calif. and Andijk, The Netherlands.

1. Double, rose-shaped, red and white flowers;
2. Semi-compact, upright, outwardly spreading and mounded plant habit; and
3. Free flowering, good basal branching and moderately vigorous growth habit.

DESCRIPTION OF PHOTOGRAPHS

This new *Impatiens* plant is illustrated by the accompanying photographs which show overall plant habit including blooms, buds, and foliage of the plant; the colors shown are as true as can be reasonably obtained by conventional photographic procedures. The photographs are of a whole plant about 10 to 12 weeks old, grown in a greenhouse in Hillscheid, Germany during the spring. The photographs were taken in May 2006.

DESCRIPTION OF THE NEW CULTIVAR

Figure 1:
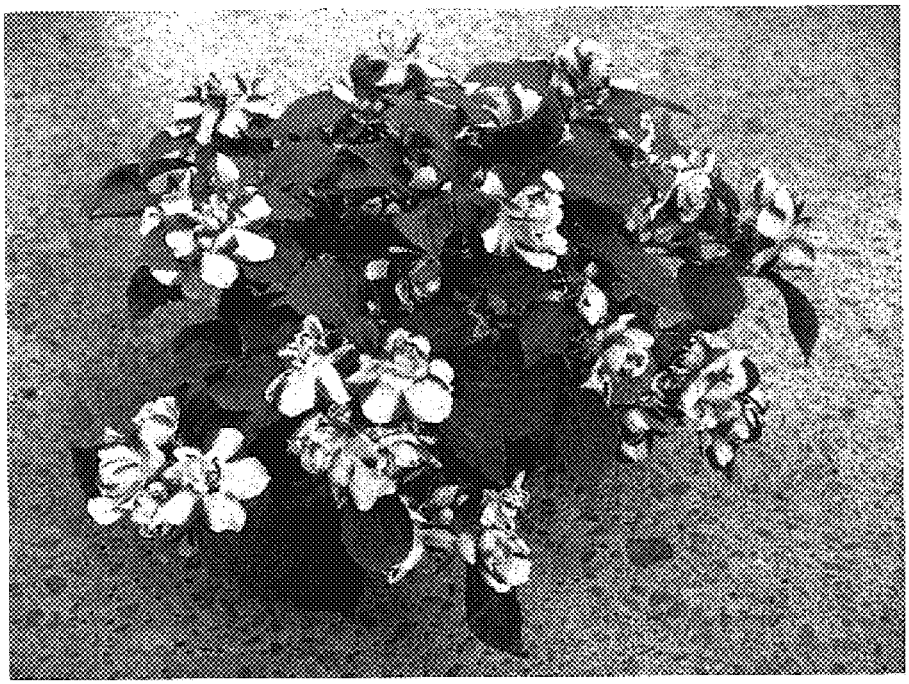
FIG. 1 shows the overall plant habit including blooms, buds, and foliage.
Figure 2:
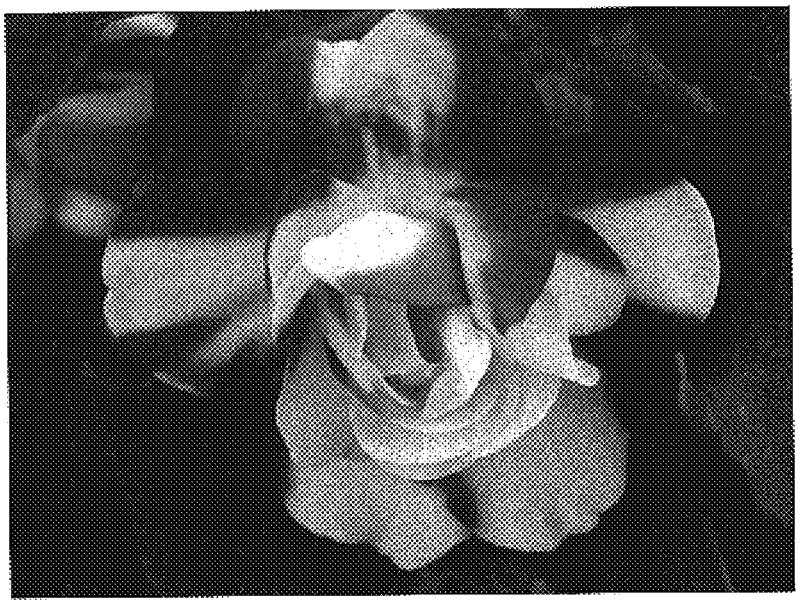
FIG. 2 shows a close-up of the mature flower.

The following detailed descriptions set forth the distinctive characteristics of 'Silte Redsar'. The data which defines these characteristics were collected from asexual reproductions carried out in Gilroy, Calif. in a trail setting. The plant history was taken on 26-week old plants grown in 6-inch containers in a greenhouse during the fall and winter seasons. The plants had one plant growth regulator treatment and one terminal pinch after cuttings were transplanted. Color readings were taken under natural light in the greenhouse in January. Color references are primarily to the R.H.S. Colour Chart of The Royal Horticultural Society of London (R.H.S.) (2001). Texture description data was viewed with a dissecting microscope.

DETAILED BOTANICAL DESCRIPTION OF THE NEW PLANT

Classification:
*Family.*—Balsaminaceae.
*Botanical.*—*Impatiens walleriana.*
*Common name.*—Impatiens.

Parentage:
*Female parent.*—'ID04-377-1' a proprietary red star-flowered *Impatiens* plant (unpatented).
*Male parent.*—'ID03-19-13', a proprietary red star-flowered *Impatiens* plant (unpatented).

Growth:

*Form.*—Semi-compact, upright, outwardly spreading and mounded plant habit.

*Growth and branching habit.*—Free flowering, good basal branching, moderately vigorous, pinching of the terminal apices enhances branching.

*Height* (*from soil level to top of blooms*).—15.0 cm to 18.0 cm.

*Width* (*including flower*).—40.0 cm to 45.0 cm.

*Time to produce a finished flowering plant.*—About 8 to 10 weeks for a 4-inch pot.

*Outdoor plant performance.*—Use in shade to semi-shade, use in hanging baskets, mixed containers, window boxes and mass plantings.

*Time to initiate and develop roots.*—Approximately 16 to 22 days at 22° C.

*Root description.*—Fibrous, fleshy, white.

Branches:

*Stem.*—Color: RHS 147C. Length: 25.0 cm to 30.0 cm. Diameter: 0.5 cm. Internode length: 0.5 cm to 1.0 cm. Texture: Glabrous.

*Peduncle.*—Color: Between RHS 144B and RHS 144C. Length: 3.1 cm to 3.3 cm. Diameter: 0.15 cm to 2.0 cm. Texture: Glabrous.

Leaves:

*Arrangement.*—Mostly alternate in whorls.

*Size.*—Length: 3.7 cm to 4.2 cm. Width: 2.7 cm to 3.2 cm.

*Shape.*—Broadly elliptical.

*Apex.*—Caudate.

*Base.*—Attenuate.

*Margin: Crenate with cilation.*

*Color* (*immature leaves*).—Upper surface: Closest to RHS 139A but darker. Lower surface: RHS 146B with RHS 182C irregular blotches of anthocyanin.

*Color* (*mature leaves*): Upper surface: Closest to RHS 138A but darker. Lower surface: RHS 146B with RHS 183C irregular blotches of anthocyanin.

*Texture.*—Glabrous.

*Venation color.*—RHS 144B.

*Petioles.*—Length: 1.9 cm to 3.5 cm. Diameter: 0.2 cm to 0.3 cm. Color: RHS 144B. Texture: Glabrous.

Flower buds:

*Shape.*—Ovate.

*Size.*—Length: 1.0 cm to 1.4 cm. Diameter: 1.0 cm to 1.1 cm.

*Color at tight bud.*—RHS 43A.

Inflorescence:

*Blooming habit.*—Continuous and freely, all through the year depending on light levels.

*Type.*—Raceme in leaf axis.

*Number of flower per inflorescence.*—4 to 6.

*Lastingness of the individual blooms.*—About 5 to 7 days depending on environmental conditions.

*Fragrance.*—None.

Flowers:

*Form and shape of corolla.*—Double-type, rose-shaped bud opening to form a full round flower.

*Corolla size.*—Width: 3.0 cm to 4.0 cm. Depth: 2.0 cm to 2.5 cm.

*Number of petals per flower.*—25 to 33.

Petals:

*Shape.*—Broadly elliptical to obovate.

*Apex.*—Retuse to emarginate.

*Base.*—Attenuate.

*Margin.*—Entire.

*Petal size.*—Length: 2.0 cm to 2.2 cm. Width: 1.7 cm to 2.1 cm.

*Color.*—Immature petals: Upper surface: Base color RHS N155B but whiter; RHS 45B along the margins at the sides only. Lower surface: Base color RHS N155B but whiter; RHS 44A to RHS 44B along the margins at the sides only. Mature petals: Upper surface: Base color RHS N155B but white; RHS 45B, along the margins at the sides only; with maturity, the red fades to having more blue in the red. Lower surface: Base color RHS N155B but whiter; RHS 44A to RHS 44B along the margins at the sides only.

*Texture.*—Papillose.

Sepals:

*Quantity.*—5; 2 large sepals, 1 modified sepal with a spur and 2 small sepals.

*Texture.*—Glabrous.

*Large sepals.*—Color: Somewhat translucent but closest to RHS N155D with an RHS 143C keel. Length: 0.7 cm to 1.5 cm. Width: 0.7 cm to 1.1 cm. Shape: Ovate. Apex: Cuspidate. Base: Fused. Margin: Entire. Spur: Color: RHS 144C. Length: 2.5 cm to 2.7 cm. Diameter: 0.1 cm.

*Small sepals.*—Color: RHS 144D; RHS 144A at the apex. Length: 0.2 cm. Width: 0.1 cm. Shape: Ovate. Apex: Acute. Margin: Entire. Base: Fused.

Reproductive organs. —Usually not developed and observed.

Fruit and seed set: No seed set observed.

Disease and insect resistance: No particular resistance or susceptibility has been observed.

COMPARISON WITH PARENTAL AND COMMERCIAL CULTIVARS

'Silte Redsar' differs from the female parent 'ID04-377-1' (unpatented) in that 'Silte Redsar' has a double flower, while 'IC04-377-1' has a single flower. Additionally, 'Silte Redsar' has lighter-colored foliage and a more compact plant habit with more vigorous growth than 'ID04-377-1'.

'Silte Redsar' differs from the male parent 'ID03-19-13' (unpatented), by having more petals per flower than 'ID03-19-13'. Additionally, 'Silte Redsar' has lighter-colored foliage and a more compact plant habit with more vigorous growth then 'ID03-19-13'.

'Silte Redsar' differs from the commercial cultivar 'Balfiespray' (U.S. Plant Pat. No. 14,675) in that 'Silte Redsar' has shorter internodes, darker branches, and wider and greener leaves than 'Balfiespray'. Additionally, 'Silte Redsar' has redder and smaller flowers than 'Balfiespray'.

I claim:

1. A new and distinct cultivar of *Impatiens* plant as shown and described herein.

* * * * *